US009436797B2

(12) United States Patent
Park et al.

(10) Patent No.: US 9,436,797 B2
(45) Date of Patent: Sep. 6, 2016

(54) BIOINFORMATICS PLATFORM FOR HIGH-THROUGHPUT IDENTIFICATION AND QUANTIFICATION OF N—GLYCOPEPTIDE

(71) Applicant: Korea Basic Science Institute, Yuseong-gu, Daejeon (KR)

(72) Inventors: Gun Wook Park, Cheongwon-Chungcheongbuk-do (KR); Jong Shin Yoo, Seoul (KR); Jin Young Kim, Cheongwon-gun Chungcheongbuk-do (KR); Ju Yeon Lee, Daejeon (KR); Hyun Kyoung Lee, Daejeon (KR); Hyun Joo An, Daejeon (KR); Jae-Han Kim, Daejeon (KR)

(73) Assignee: Korea Basic Science Institute (KR)

( * ) Notice: Subject to any disclaimer, the term of this patent is extended or adjusted under 35 U.S.C. 154(b) by 560 days.

(21) Appl. No.: 13/884,233

(22) PCT Filed: Jan. 22, 2013

(86) PCT No.: PCT/KR2013/000496
§ 371 (c)(1),
(2) Date: May 8, 2013

(87) PCT Pub. No.: WO2014/051220
PCT Pub. Date: Apr. 3, 2014

(65) Prior Publication Data
US 2015/0186595 A1   Jul. 2, 2015

(30) Foreign Application Priority Data

Sep. 27, 2012   (KR) ........................ 10-2012-0108011

(51) Int. Cl.
| | |
|---|---|
| *G06F 19/16* | (2011.01) |
| *G06F 19/24* | (2011.01) |
| *H01J 49/26* | (2006.01) |
| *G01N 33/68* | (2006.01) |
| *C12Q 1/37* | (2006.01) |
| *H01J 49/00* | (2006.01) |
| *G01N 30/86* | (2006.01) |
| *G01N 30/88* | (2006.01) |

(52) U.S. Cl.
CPC ............... *G06F 19/16* (2013.01); *C12Q 1/37* (2013.01); *G01N 30/86* (2013.01); *G01N 33/6848* (2013.01); *H01J 49/004* (2013.01); *H01J 49/0027* (2013.01); *G01N 2030/8813* (2013.01); *G01N 2030/8831* (2013.01); *G01N 2400/00* (2013.01); *G01N 2440/38* (2013.01); *G01N 2560/00* (2013.01); *G01N 2570/00* (2013.01); *H01J 49/0036* (2013.01)

(58) Field of Classification Search
None
See application file for complete search history.

(56) References Cited

U.S. PATENT DOCUMENTS

| 8,227,251 B2 | 7/2012 | Ranish et al. | |
|---|---|---|---|
| 2004/0248317 A1* | 12/2004 | Swamy | G01N 33/6842 436/173 |
| 2008/0050833 A1 | 2/2008 | Smith et al. | |
| 2009/0053742 A1 | 2/2009 | Gygi et al. | |

FOREIGN PATENT DOCUMENTS

| KR | 20100088217 | 8/2010 |
|---|---|---|
| WO | 2014051220 | 4/2014 |

OTHER PUBLICATIONS

Breidenbach et al., "Mapping Yeast N-Glycosites with Isotopically Recorded Glycans," Molecular & Cellular Proteomics, 2012, vol. 11, No. 6, pp. 1-10.
Farrah et al., "A High-Confidence Human Plasma Proteome Reference Set with Estimated Concentrations in PeptideAtlas," Molecular and Cellular Proteomics, 2011.
Godlberg, et al., "Automated N-Glycopeptide Identification Using a Combination of Single—and Tandem—MS," Journal of Proteome Research, 2007, 6(10), pp. 3995-4005.
International Search Report and Written Opinion for PCT/KR2013/000496 dated May 29, 2013.
Rebecchi et al., "Label-Free Quantitation: A New Glycoproteomics Approach," Journal of the American Society for Mass Spectrometry, 2009, 20(6), pp. 1048-1059.
Ruiz-May et al., "Analytical Technologies for Identification and Characterization of the Plant N-Glycoproteome," Frontier in Plant Science, Jul. 2012, vol. 3, No. 150, pp. 1-8.
C. A. Cooper, E. Gasteiger and N. H. Packer, GlycoMod—a software tool for determining glycosylation compositions from mass spectrometric data, Proteomics, 2001, 1, 340-349.
E. P. Go, K. R. Rebecchi, D. S. Dalpathado, M. L. Bandu, Y. Zhang and H. Desaire, GlycoPep DB: a tool for glycopeptide analysis using a "smart search", Anal. Chem., 2007, 79, 1708-1713.
N. Deshpande, P. H. Jensen, N. H. Packer and D. Kolarich, GlycoSpectrumScan: fishing glycopeptides from MS spectra of protease digests of human colostrum sIgA, J. Proteome Res., 2010, 9, 1063-1075.
A. Ceroni, K. Maass, H. Geyer, R. Geyer, A. Dell and S. M. Haslam, GlycoWorkBench: a tool for the computerassisted annotation of mass spectra of glycans, J. Proteome Res., 2008, 7, 1650-1659.
K. Maass, R. Ranzinger, H. Geyer, C. W. von der Lieth and R. Geyer, "Glyco-peakfinder"—de novo composition analysis of glycoconjugates, Proteomics, 2007, 7, 4435-4444.
J. Irungu, E. P. Go, D. S. Dalpathado and H. Desaire, Simplification of mass spectral analysis of acidic glycopeptides using GlycoPep ID, Anal. Chem., 2007, 79, 3065-3074.

(Continued)

*Primary Examiner* — John S Brusca
(74) *Attorney, Agent, or Firm* — Workman Nydegger

(57) ABSTRACT

The present invention relates to a more efficient and accurate method for the identification and quantification of comparatively low abundant glycopeptides, compared with general peptides, using mass spectrum obtained by using high resolution mass spectrometer. Therefore, the method of the present invention can be effectively used for the techniques for identification of biotherapeutics and diagnosis of cancer or disease by screening glycopeptide, the disease marker (Biomarker), from various samples.

14 Claims, 14 Drawing Sheets
(9 of 14 Drawing Sheet(s) Filed in Color)

(56) References Cited

OTHER PUBLICATIONS

O. Ozohanics, J. Krenyacz, K. Lud'anyi, F. Pollreisz, K. V'ekey and L. Drahos, GlycoMiner: a new software tool to elucidate glycopeptide composition, Rapid Commun. Mass Spectrom., 2008, 22, 3245-3254.

P. Pompach, K. Chandler, R. Lan, N. Edwards and R. Goldman, Semi-automated identification of N-glycopeptides by hydrophilic interaction chromatography, nano-reverse-phase LC-MS/MS, and glycan database search, J. Proteome Res., 2012, 11, 1728-1740.

Y. Wu, Y. Mechref, I. Klouckova, A. M. Mayampurath, M. V. Novotny and H. Tang, Mapping site-specific protein N-glycosylations through liquid chromatography/mass spectrometry and targeted tandem mass spectrometry, Rapid Commun. Mass Spectrom., 2010, 24, 965-972.

A. M. Mayampurath, Y. Wu, Z. M. Segu, Y. Mechref and H. Tang, Improving confidence in detection and characterization of protein N-glycosylation sites and microheterogeneity, Rapid Commun. Mass Spectrom., 2011, 25, 2007-2019.

C. L. Woodin, D. Hua, M. Maxon, K. R. Rebecchi, E. P. Go and H. Desaire, GlycoPep Grader: a web-based utility for assigning the composition of N-linked glycopeptides, Anal. Chem., 2012, 84, 4821-4829.

Zhikai Zhu, David Hua, Daniel F. Clark, Eden P. Go, and Heather Desaire, GlycoPep Detector: A tool for assigning mass spectrometry data of N-linked glycopeptides based on their ETD spectra, Anal. Chem., 2013.

* cited by examiner

BIOINFORMATICS PLATFORM FOR HIGH-THROUGHPUT IDENTIFICATION AND QUANTIFICATION OF N—GLYCOPEPTIDE

CROSS-REFERENCE TO RELATED APPLICATIONS

This application is a U.S. Nationalization of PCT Application No. PCT/KR2013/000496 filed on 22 Jan. 2013, entitled "Bioinformatics Platform for High-Throughput Identification and Quantification of N Glycopeptide." PCT Application No. PCT/KR2013/000496 claims the benefit of and priority to Korean Patent App. No. 10-2012-0108011, which was filed on 27 Sep. 2012. The above listed applications are incorporated herein by reference in their entireties.

BACKGROUND OF THE INVENTION

1. Field of the Invention

The present invention relates to a novel bioinformatics platform for identification and quantification of N-linked glycopeptide based on mass spectrometry.

2. Description of the Related Art

Human blood is a mixture of various proteins, among which at least 50% are glycoproteins. However, it is often not possible to characterize all glycopeptides in a sample because of the high complexity and diversity of glycoprotein samples, and the relative lower mass spectrometry intensities of glycopeptides in comparison to the non-glycopeptides. Ever since high resolution mass spectrometer was introduced, the analysis of glycan and glycoprotein has been advancing fast. Nevertheless, bioinformatics techniques necessary for the identification and quantification of glycoproteins are not yet up to date. It is known that many therapeutic proteins are glycosylated in a variety of forms and in very complicated ways. There are two main ways of techniques for the identification and quantification of glycosylation of such glycoproteins. One way is the identification and quantification of glycan by using chemical cleavage induced by an enzyme or a compound, and the other way is the identification and quantification of glycopeptide. However, the method for analyzing released glycan has a problem of not knowing glycosylation site-specific information. Should glycopeptide can be identified and quantified as it is, not only tumor identification and progression can be checked but also huge information on glycosylation site and N-linked sugar chain size and the numbers of growing side chain in addition to glycoprotein itself can be obtained.

In general, the method for analyzing glycosylation of glycoprotein includes the step of concentration of glycoprotein at protein level. But in this invention, a standard glycoprotein sample was used to execute and complete this invention. Particularly, peptides and glycopeptides were obtained by hydrolyzing the said standard glycoprotein sample with trypsin. Then, those peptides were analyzed with high resolution mass spectrometer. The results of tandem mass spectrum (MS/MS) and mass spectrum (MS) were compared with glycopeptide database to identify and quantify the glycopeptides.

The recent softwares for the screening of glycopeptide using MS/MS or MS are exemplified by Peptoonist (David Goldberg., et. al; Automated N-Glycopeptide Identification Using a Combination of Single- and Tandem-MS. Journal of proteome research 2007, 6, 3995-4005), SimGlycan (glycotools.qa-bio.com/SimGlycan), GlycoMiner (Oliver Ozohanics., et., al; GlycoMiner: a new software tool to elucidate glycopeptide composition. Rapid Communications in Mass Spectrometry 2008, 22, 3245-3254), GlycoSpectrumScan (NandanDeshpande., et., al; GlycoSpectrumScan: Fishing Glycopeptides from MS Spectra of Protease Digests of Human Colostrum sIgA. Journal of proteome research 2010, 9, 1063-1075), GlycoPep Grader (Carrie L. Woodin. et., al; GlycoPep Grader: A Web-Based Utility for Assigning the Composition of N-Linked Glycopeptides. Analytical Chemistry, 2012), etc.

Since the above software programs were designed to identify glycopeptide by using tandem mass spectrum alone, there is a doubt in accurate profiling of glycopeptide and also inconsistency in the quantitative analysis results is another problem. It has been an issue for them not to support various high resolution mass spectrometers.

To overcome the above problems, the present inventors studied and completed a novel method for more efficient identification and quantification of comparatively low abundant glycopeptides, compared with general peptides, using mass spectrum. First of all, glycopeptides of 281 glycoproteins (Terry Farrah., et., al.; A High-Confidence Human Plasma Proteome Reference Set with Estimated Concentrations in PeptideAtlas. Molecular Cell Proteomics, 2011) existing at high concentration in human serum were stored, followed by modeling of theoretical isotopic distribution of such glycopeptides. The obtained results proceeded to database. In this invention, isotopic distribution of glycopeptide was obtained by using MS/MS and MS as well, which was compared with glycopeptide database to identify glycopeptide accurately and to quantify such glycopeptide by calculating area in ion chromatograms.

SUMMARY OF THE INVENTION

It is an object of the present invention to provide a bioinformatics platform for more efficient and accurate identification and quantification of comparatively low abundant glycopeptides, compared with general peptides, using mass spectrum results.

To achieve the above object, the present invention provides a novel bioinformatics platform for the identification and quantification of N-linked glycopeptide from glycoprotein, which comprises the following steps:

obtaining mass spectrum by analyzing polypeptides prepared by hydrolyzing glycoproteins with protease by using high resolution mass spectrometer (step 1);

converting the mass spectrum obtained in step 1 into MS1 (Mass spectrum 1) and tandem spectrum (MS/MS) (step 2);

calculating M-score at each tandem spectrum selected from the group consisting of converted tandem spectrums showing Oxonium ion peak molecular weights of 129.06, 138.06, 145.05, 147.07, 163.06, 168.07, 186.08, 204.08, 274.09, 292.10, 350.15, 366.14, 454.16, 528.19, and 657.24 (step 3);

selecting glycopeptide spectrum using the M-score obtained in step 3 (step 4);

obtaining isotopic distribution in MS1 of the glycopeptide spectrum selected in step 4, which is compared with the database to calculate S-score, and then identifying glycopeptide candidates by using the calculated S-score (step 5);

evaluating exact glycopeptide from the glycopeptide candidates identified in step 5 by using E-score, Y-score, and Y'-score in tandem spectrum (step 6);

performing quantitative analysis with the glycopeptides evaluated in step 6 (step 7); and performing additional identification and quantification of family N-linked glycopeptide via correlation analysis with those glycopeptides quantified in step 6 (step 8).

Advantageous Effect

As explained hereinbefore, the present invention provides a more efficient and accurate method for quantification of glycopeptide having specific sugar chain in a variety of samples, and hence this method can be effectively used for the techniques for prediction and diagnosis of cancer or disease by screening disease marker from various samples. This method is also useful for those who want to analyze glycopeptide and glyco-structure of glycoprotein biosimiliar therapeutics with high resolution mass spectrometer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The application of the preferred embodiments of the present invention is best understood with reference to the accompanying drawings, wherein.

DESCRIPTION OF THE PREFERRED EMBODIMENTS

Figure 1:
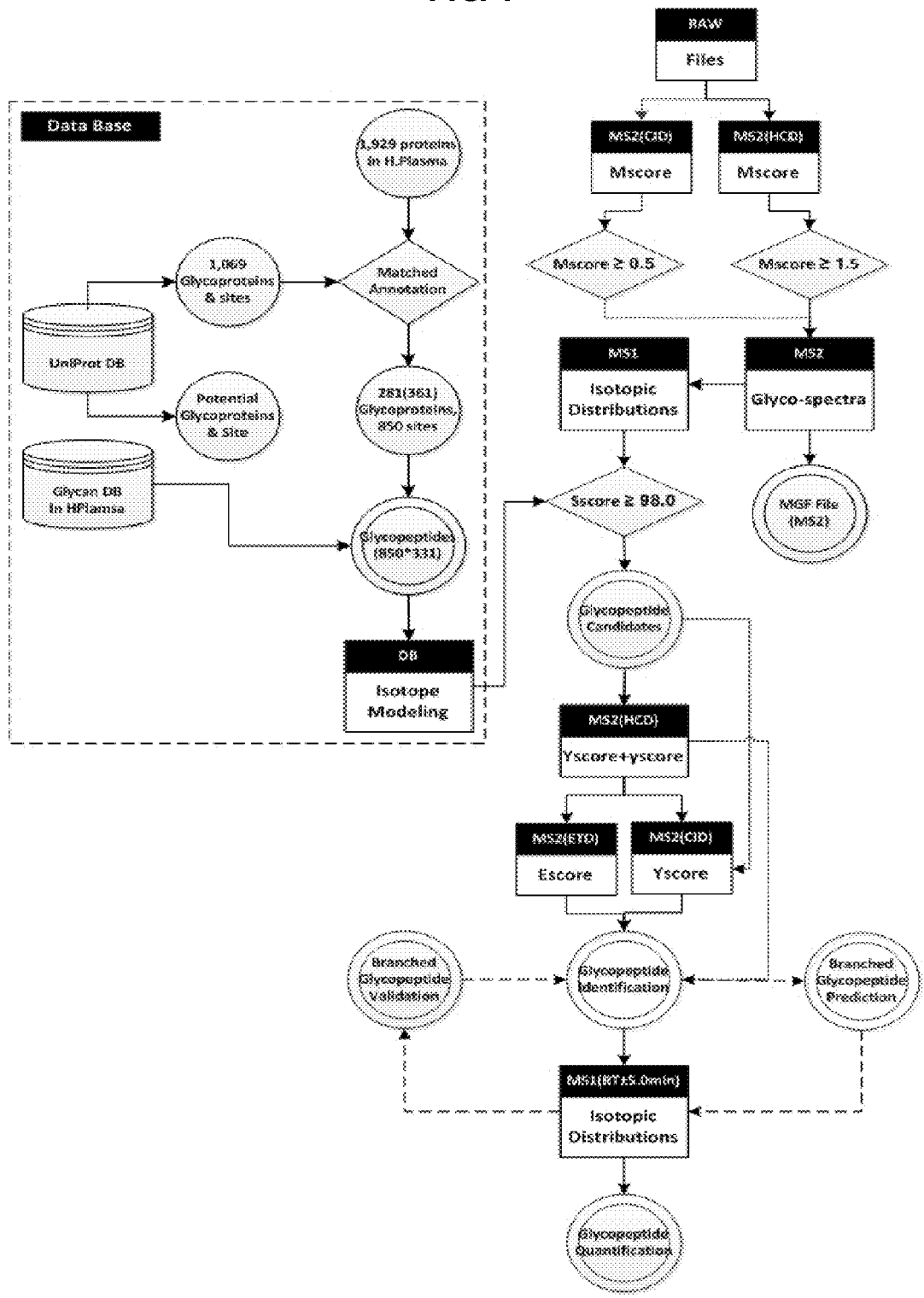
FIG. 1 is a flow chart illustrating the novel bioinformatics platform for the identification and quantification of N-linked glycopeptide from samples.

To describe this invention in more detail, the terms used in this description are defined as follows:

"Protease" indicates the enzyme that cuts the amino acid bond of glycoprotein containing glucose to give a peptide mixture.

"Tandem mass spectrometry" is the method for analyzing mass of spectrum (MS/MS) of selected ions of interest ones or of high abundant ions from total mass spectrum (MS).

"Isotopes" indicate chemical elements having the same atomic number but different atomic weights.

"Isotope Grouping" indicates the grouping of those isotopes identified from the peak list obtained from experiments.

"N-glycopeptide Isotopic Modeling" indicates the theoretical isotopic distribution of glycopeptides established from the database.

"S-score (Similarity Score)" indicates the numerical value representing similarity between the isotope peak distribution obtained from experiments and the isotope peak distribution theoretically presumed from the database.

"Delta" indicates the absolute value representing the difference between the theoretical mass and the real mass confirmed from experiments.

Hereinafter, the present invention is described in detail.

The present invention provides a novel bioinformatics platform for the identification and quantification of N-linked glycopeptide from glycoprotein, which comprises the following steps:

obtaining mass spectrum by analyzing polypeptides prepared by hydrolyzing glycoproteins with protease by using high resolution mass spectrometer (step 1);

converting the mass spectrum obtained in step 1 into MS1 (Mass spectrum 1) and tandem spectrum (MS/MS) (step 2);

calculating M-score at each tandem spectrum selected from the group consisting of converted tandem spectrums showing Oxonium ion peak molecular weights of 129.06, 138.06, 145.05, 147.07, 163.06, 168.07, 186.08, 204.08, 274.09, 292.10, 350.15, 366.14, 454.16, 528.19, and 657.24 (step 3);

selecting glycopeptide spectrum using the M-score obtained in step 3 (step 4);

obtaining isotopic distribution in MS1 of the glycopeptide spectrum selected in step 4, which is compared with the database to calculate S-score, and then identifying glycopeptide candidates by using the calculated S-core (step 5);

evaluating exact glycopeptide from the glycopeptide candidates identified in step 5 by using E-score, Y-score, and Y'-score in tandem spectrum (step 6);

performing quantitative analysis with the glycopeptides evaluated in step 6 (step 7); and performing additional identification and quantification of family N-glycopeptide via correlation analysis with those glycopeptides quantified in step 6 (step 8).

The present invention also provides a bioinformatics platform for more accurate and efficient identification and quantification of glycopeptide via comparison of isotopic distributions. Particularly the present invention provides a method for accurate identification of glycopeptide by using isotopic distribution after obtaining glycopeptide spectrum by using M-score and by confirming and evaluating the glycopeptide again by using Y-, E-, or Y'-score.

Hereinafter, the Examples of the present invention are described in more detail step by step using FIG. 1 as a reference.

In a preferred embodiment of the present invention, glycopeptide is identified and quantified by the method comprising the following steps, but not always limited thereto:

1) obtaining mass spectrum of polypeptide prepared by hydrolyzing glycoprotein with trypsin by analyzing with high resolution mass spectrometer Orbitrap;

2) converting the mass spectrometer RAW file obtained in step 1 into ms1(TXT) file format by using RawExtractor v1.9, which is converted further into ms2 (MGF) file format by using MM File Conversion Tools v3.9;

3) calculating M-score from each HCD (High energy Collision Dissociation) spectrum of the ms2 (MGF) file converted in step 2;

4) selecting glycopeptide spectrum that acquires at least 1.5 M-score among those obtained in step 3;

5) obtaining isotopic distribution in MS1 of the glycopeptide spectrum selected in step 4, which is compared with the database, leading to the identification of glycopeptide candidate acquiring at least 98.0 S-score;

6) evaluating glycopeptide accurately by using Y'-score in HCD spectrum and Y-score in CID (Collision Induced Dissociation) spectrum of those glycopeptide candidates identified in step 5;

7) performing quantitative analysis with the glycopeptides identified in step 6; and 8) performing additional identification and quantification of family N-glycopeptide via correlation analysis with the glycopeptides identified in step 6.

In another preferred embodiment of the present invention, glycopeptide is preferably identified and quantified by the method comprising the following steps, but not always limited thereto:

1) obtaining mass spectrum of polypeptide prepared by hydrolyzing glycoprotein with trypsin by analyzing with high resolution mass spectrometer Orbitrap;

2) converting the mass spectrometer RAW file obtained in step 1 into ms1(TXT) file format by using RawExtractor v1.9, which is converted further into ms2 (MGF) file format by using MM File Conversion Tools v3.9;

3) calculating M-score from each HCD (High energy Collision Dissociation) spectrum of the ms2 (MGF) file converted in step 2;

4) selecting glycopeptide spectrum that acquires at least 1.5 M-score among those obtained in step 3;

5) obtaining isotopic distribution in MS1 of the glycopeptide spectrum selected in step 4, which is compared with the database, leading to the identification of glycopeptide candidate acquiring at least 98.0 S-score;

6) evaluating glycopeptide accurately by using Y'-score in HCD spectrum and E-score in ETD (Electron Transfer Dissociation) spectrum of those glycopeptide candidates identified in step 5;

7) performing quantitative analysis with the glycopeptides identified in step 6; and 8) performing additional identification and quantification of family N-glycopeptide via correlation analysis with the glycopeptides identified in step 6.

In another preferred embodiment of the present invention, glycopeptide is preferably identified and quantified by the method comprising the following steps, but not always limited thereto.

In another preferred embodiment of the present invention, glycopeptide is preferably identified and quantified by the method comprising the following steps, but not always limited thereto:

1) obtaining mass spectrum of polypeptide prepared by hydrolyzing glycoprotein with trypsin by analyzing with high resolution mass spectrometer Orbitrap;

2) converting the mass spectrometer RAW file obtained in step 1 into ms1(TXT) file format by using RawExtractor v1.9, which is converted further into ms2 (MGF) file format by using MM File Conversion Tools v3.9;

3) calculating M-score from each HCD (High energy Collision Dissociation) spectrum of the ms2 (MGF) file converted in step 2;

4) selecting glycopeptide spectrum that acquires at least 1.5 M-score among those obtained in step 3;

5) obtaining isotopic distribution in MS1 of the glycopeptide spectrum selected in step 4, which is compared with the database, leading to the identification of glycopeptide candidate acquiring at least 98.0 S-score;

6) evaluating glycopeptide accurately by using Y'-score in HCD tandem spectrum of those glycopeptide candidates identified in step 5;

7) performing quantitative analysis with the glycopeptides identified in step 6; and 8) performing additional identification and quantification of family N-glycopeptide via correlation analysis with the glycopeptides identified in step 6.

In another preferred embodiment of the present invention, glycopeptide is preferably identified and quantified by the method comprising the following steps, but not always limited thereto:

1) obtaining mass spectrum of polypeptide prepared by hydrolyzing glycoprotein with trypsin by analyzing with high resolution mass spectrometer LTQ-FT;

2) converting the mass spectrometer RAW file obtained in step 1 into ms1(TXT) file format by using RawExtractor v1.9, which is converted further into ms2 (MGF) file format by using MM File Conversion Tools v3.9;

3) calculating M-score from each CID spectrum of the ms2 (MGF) file converted in step 2;

4) selecting glycopeptide spectrum that acquires at least 0.5 M-score among those obtained in step 3;

5) obtaining isotopic distribution in MS1 of the glycopeptide spectrum selected in step 4, which is compared with the database, leading to the identification of glycopeptide candidate acquiring at least 98.0 S-score;

6) evaluating glycopeptide accurately by using Y-score in CID tandem spectrum of those glycopeptide candidates identified in step 5;

7) performing quantitative analysis with the glycopeptides identified in step 6; and 8) performing additional identification and quantification of family N-glycopeptide via correlation analysis with the glycopeptides identified in step 6.

In another preferred embodiment of the present invention, glycopeptide is preferably identified and quantified by the method comprising the following steps, but not always limited thereto:

1) obtaining mass spectrum of polypeptide prepared by hydrolyzing glycoprotein with trypsin by analyzing with high resolution mass spectrometer Q-Tof;

2) converting the mass spectrometer WIFF file obtained in step 1 into ms1 (TXT) and ms2 (MGF) file format by using AB Science MS Data Convert v1.3 and ProteoWizard v2.1 (proteowizard.sourceforge.net/);

3) calculating M-score from each CID spectrum of the ms2 (MGF) file converted in step 2;

4) selecting glycopeptide spectrum that acquires at least 1.5 M-score among those obtained in step 3;

5) obtaining isotopic distribution in MS1 of the glycopeptide spectrum selected in step 4, which is compared with the database, leading to the identification of glycopeptide candidate acquiring at least 98.0 S-score;

6) evaluating glycopeptide accurately by using Y-score in CID tandem spectrum of those glycopeptide candidates identified in step 5;

7) performing quantitative analysis with the glycopeptides identified in step 6; and 8) performing additional identification and quantification of family N-glycopeptide via correlation analysis with the glycopeptides identified in step 6.

In this invention, high resolution mass spectrometer is used in order to analyze those glycopeptides qualitatively and quantitatively that are more complicated and have wide variety but exist at lower concentration than general peptides. To analyse the results obtained from mass spectrometry faster and more accurately, M-score, S-score, E-score, Y-score, and y-score are used for the identification and quantification of glycopeptide.

In the above method, using M-score, as shown in step 3, is more efficient in analyzing not only general peptide spectrum but also glycopeptide spectrum. The said M-score can be calculated by the following mathematical formula 1.

[Mathematical Formula 1]

$$M_{Score} = \frac{n}{N} * \frac{\sqrt{\sum_{i=1}^{n} O_i}}{(n-1)}$$

$$O_i = \frac{I_i}{I_{max(<700Da)}} * C/MassError + 1.0$$

(N: number of observable oxonium ions;
n: number of observed oxonium ions;
$I_i$: $i^{th}$ peak intensity in repetitive analysis; and
C: constant value).

Figure 2A:
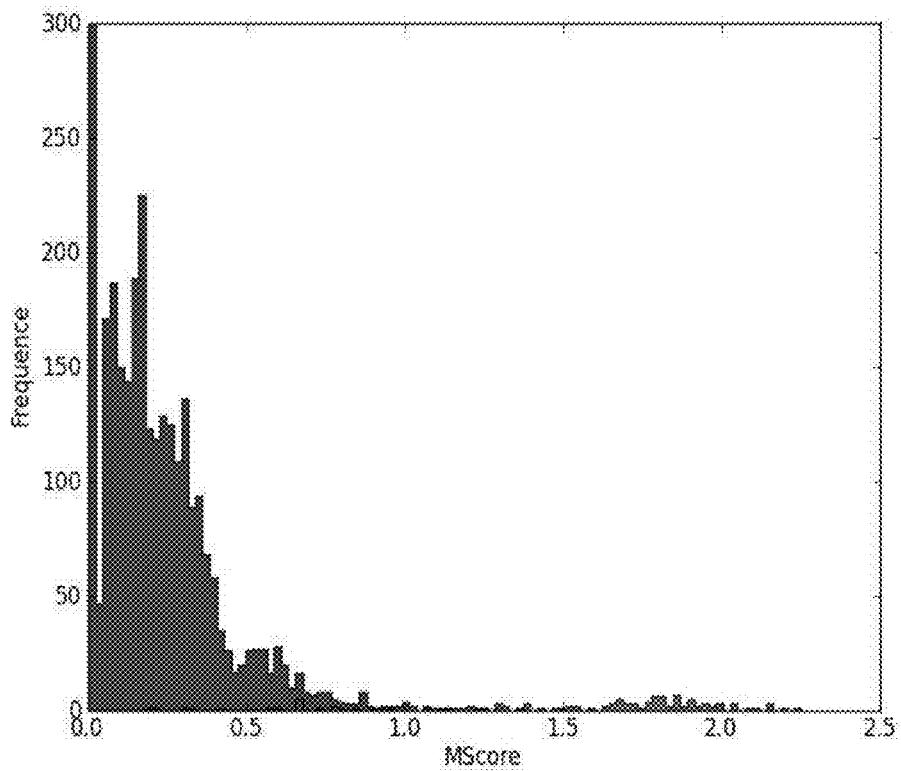
FIG. 2a is a diagram illustrating the M-score distribution of general peptides and glycopeptides according to step 2 of the bioinformatics platform for the identification and quantification of N-linked glycopeptide of an example of the present invention performed with the standard glycoprotein.
Figure 2B:
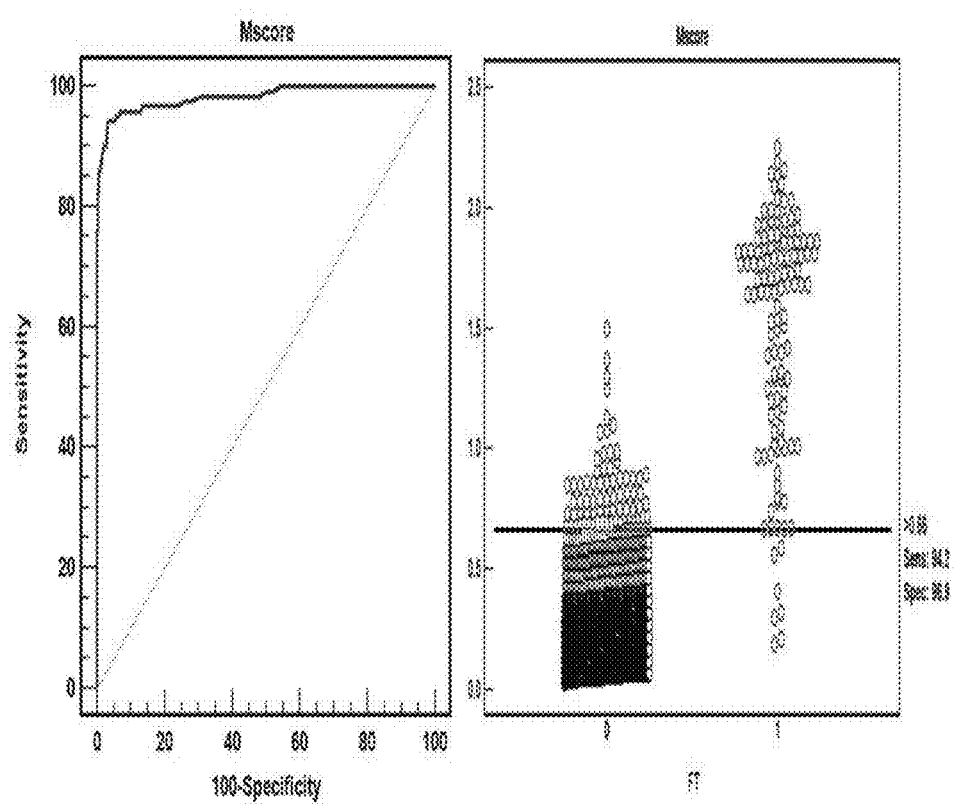
FIG. 2b is a diagram illustrating the correlation between sensitivity and specificity of general peptides and glycopeptides of step 2 of the bioinformatics platform for the identification and quantification of N-linked glycopeptide of an example of the present invention performed with the standard glycoprotein.
Figure 3:
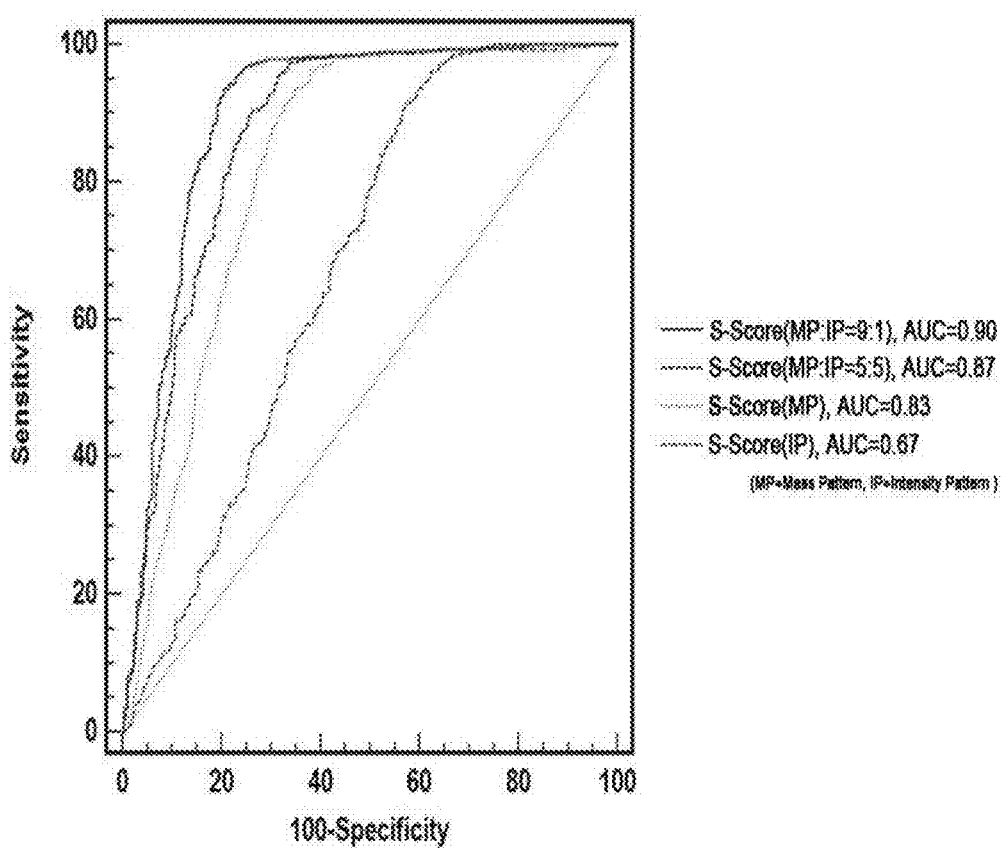
FIG. 3 is a diagram illustrating the correlation between sensitivity and specificity for the optimization of S-score obtained via comparison with the database in step 5 of the bioinformatics platform for the identification and quantification of N-linked glycopeptide of an example of the present invention performed with the standard glycoprotein.
Figure 4A:
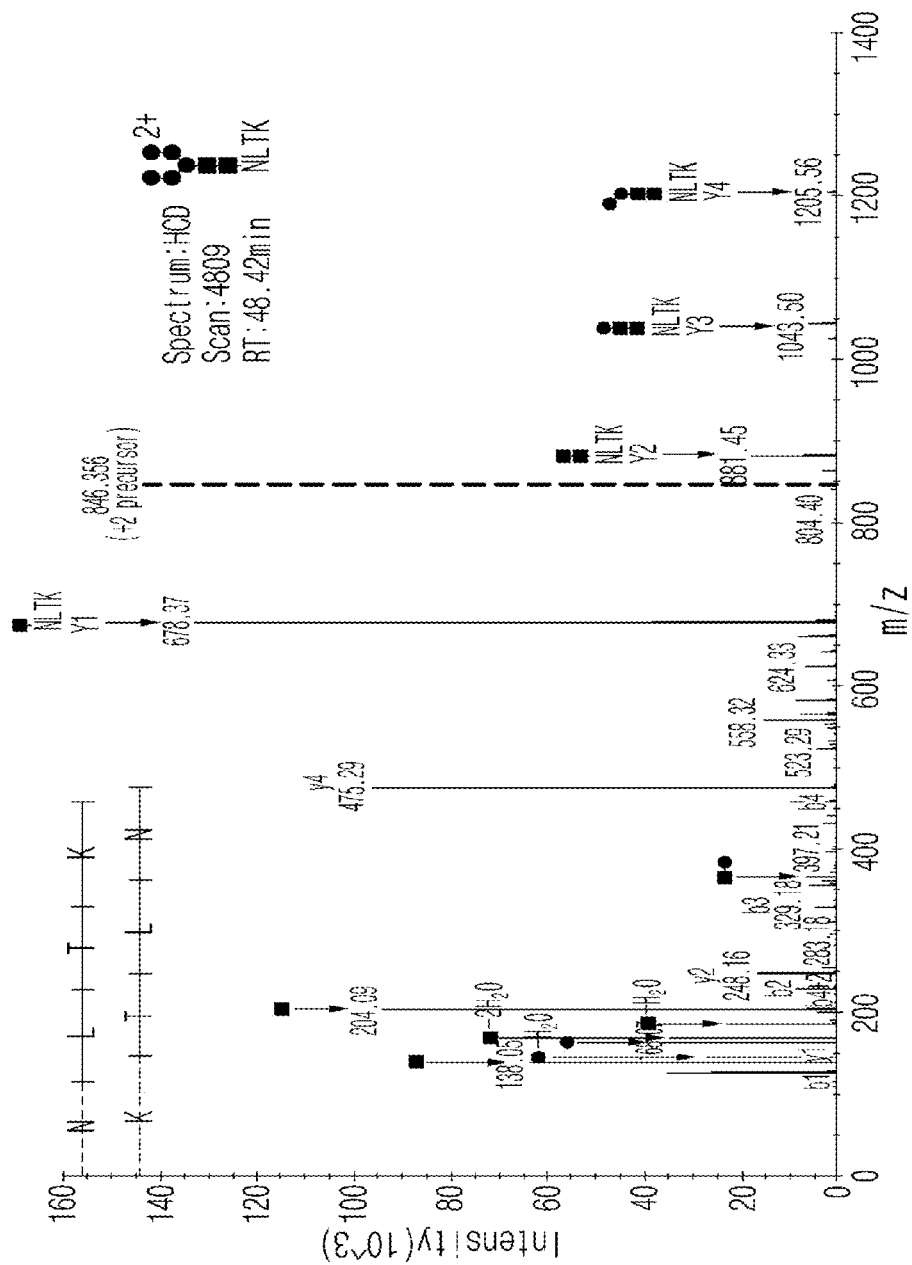
FIG. 4a is a diagram illustrating the representative HCD spectrum of NLTK_5200, among the N-linked glycopeptides identified in an example of the present invention performed with the standard glycoprotein.
Figure 4B:
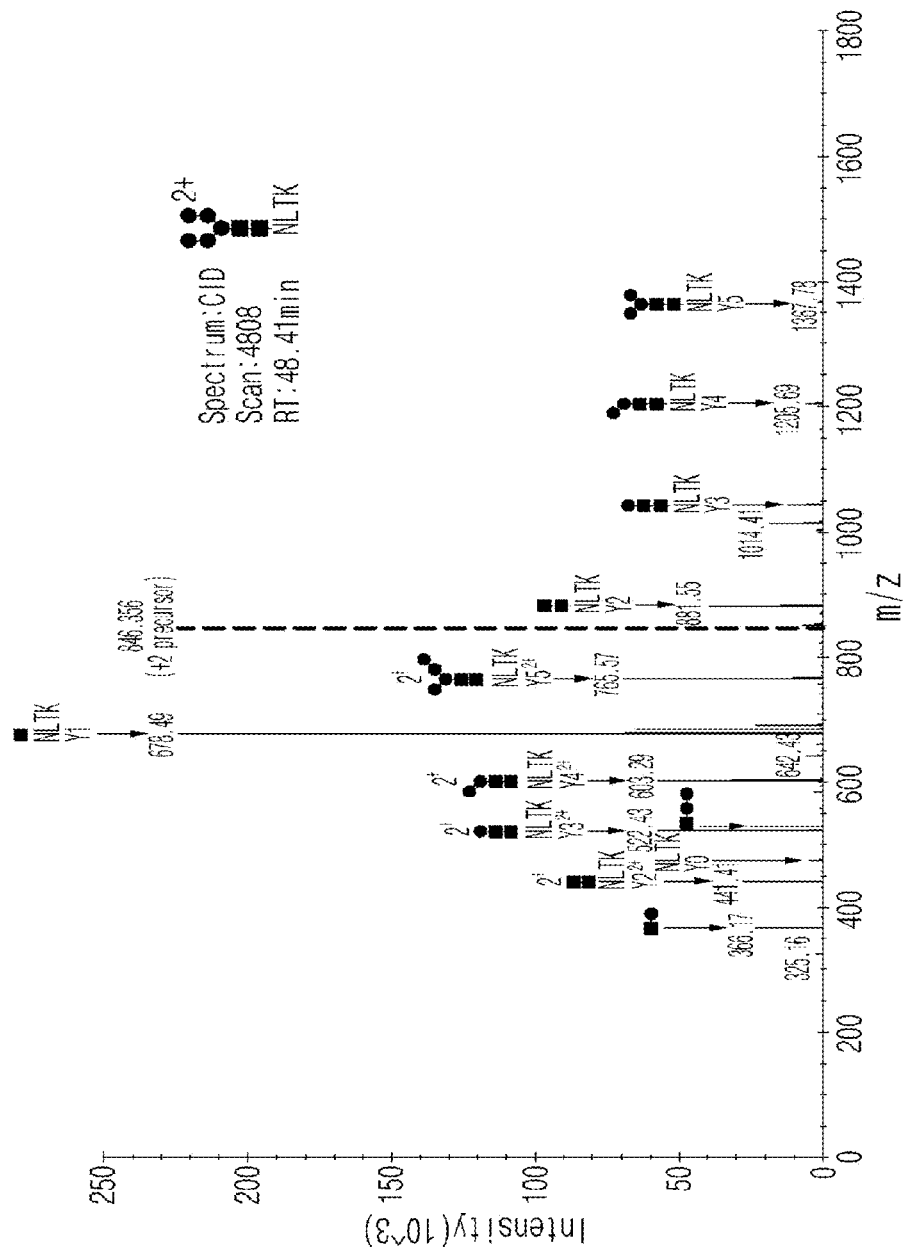
FIG. 4b is a diagram illustrating the representative CID spectrum of NLTK_5200, among the N-linked glycopeptides identified in an example of the present invention performed with the standard glycoprotein.
Figure 5A:
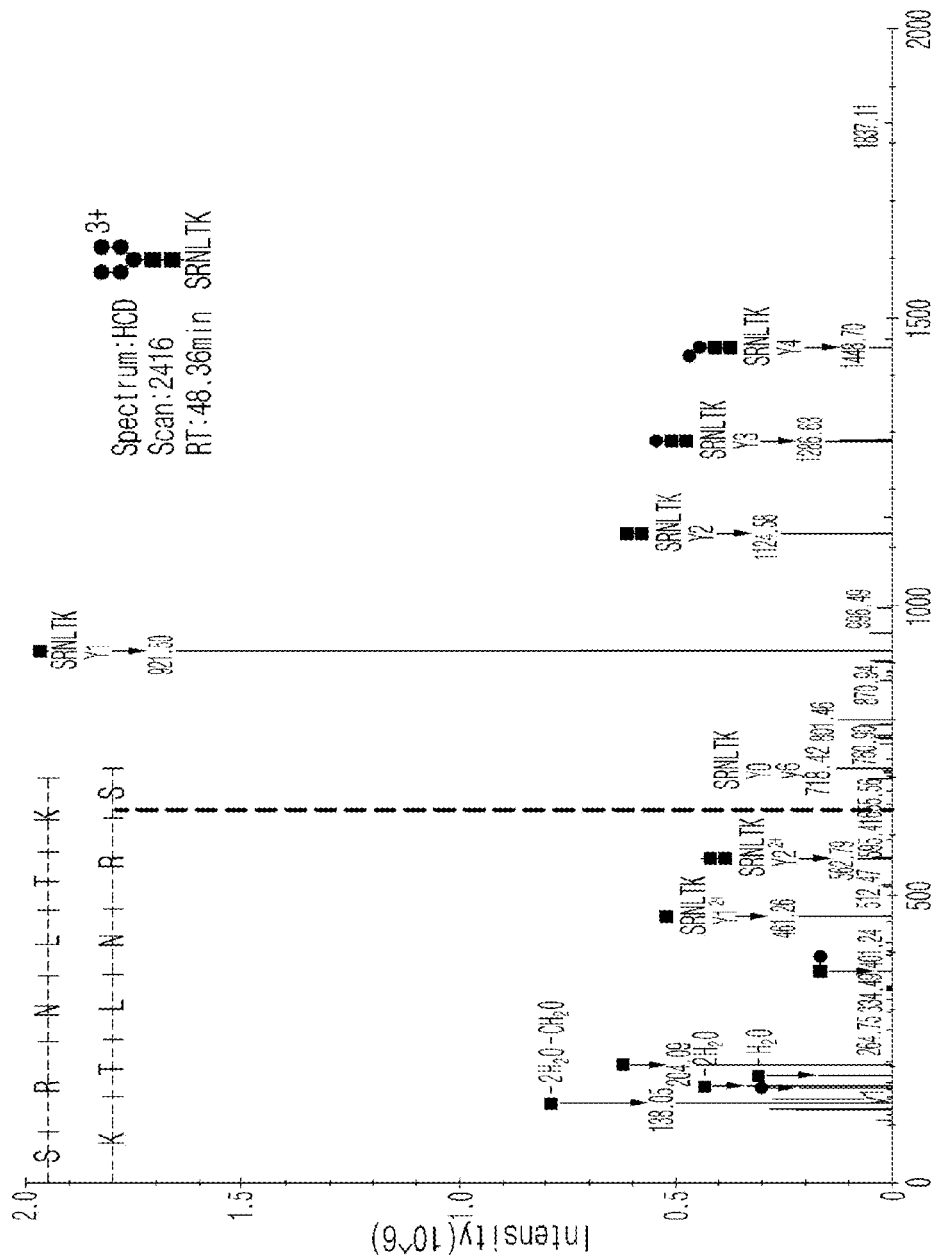
FIG. 5a is a diagram illustrating the representative HCD spectrum of SRNLTK_5200, among the N-linked glycopeptides identified in an example of the present invention performed with the standard glycoprotein.
Figure 5B:
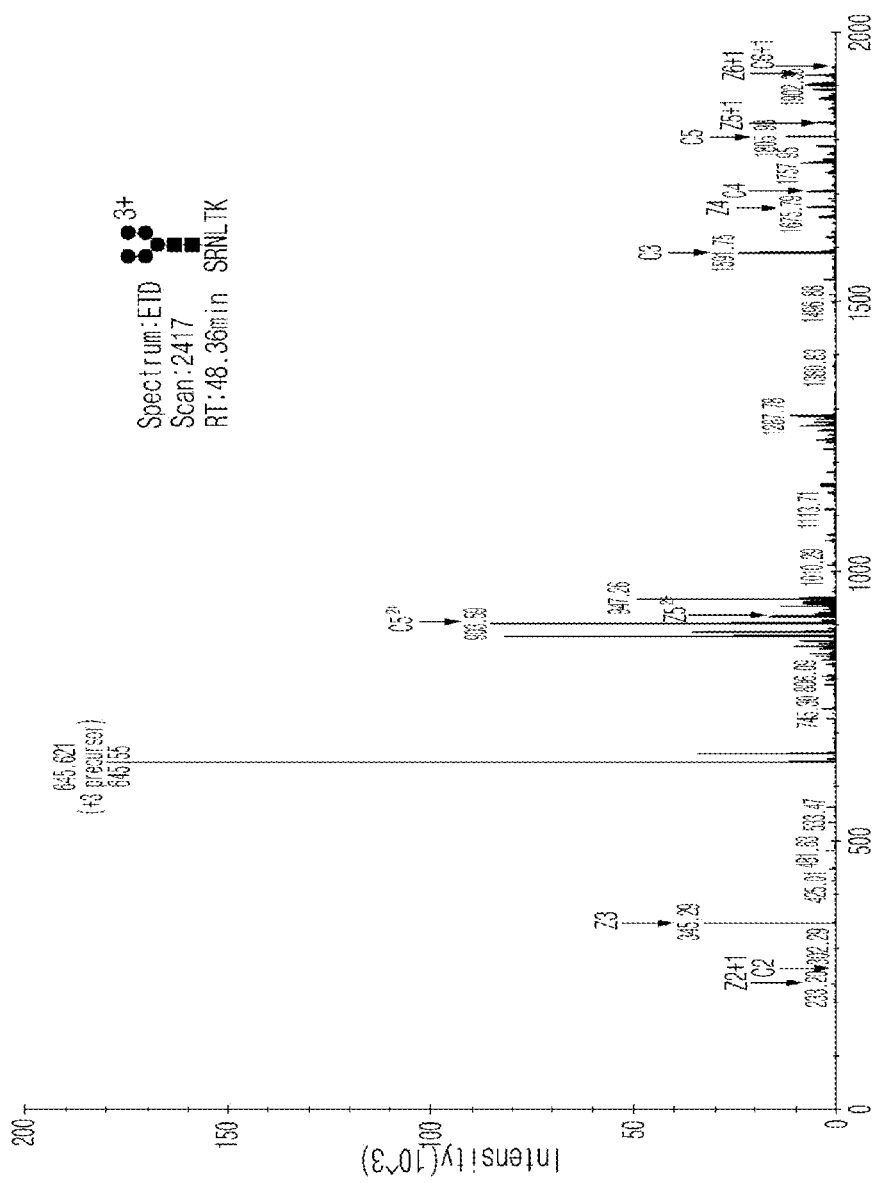
FIG. 5b is a diagram illustrating the representative ETD spectrum of SRNLTK_5200, among the N-linked glycopeptides identified in an example of the present invention performed with the standard glycoprotein.

FIG. 2a illustrates the M-score distribution map of HCD spectra of the glycoprotein standard sample (RNaseB). In this distribution map, general peptides are presented in blue color and glycopeptides are presented in green color via manual evaluation. The correlation of sensitivity and specificity between general peptides and glycopeptides is presented by ROC(Receiver Operating Characteristic) curve, which is AUC (Area Under Curve) in FIG. 2b whose value is 0.98.

In the above method, as shown in step 5, using S-score is advantageous in the identification of glycopeptide which is characterized by the screening and comparison of the theoretical isotopic distribution obtained from the database with the isotopic distribution obtained by experiments. The said S-score can be calculated by the following mathematical formula 2.

[Mathematical Formula 2]

$$S_{Score} = \left( \frac{1.0}{\left(1.0 + \sum_{i=1}^{n}(X1-Y1)_i^2\right)} * C1 \right) + \left( \frac{n(\sum X2Y2) - (\sum X2)(\sum Y2)}{\sqrt{(n\sum X2^2 - (\sum X2)^2)*(n\sum Y2^2 - (\sum Y2)^2)}} * C2 \right)$$

(X1: mass of $n^{th}$ peak among theoretical isotope peaks;
Y1: mass of $n^{th}$ peak among experimentally obtained isotope peaks;
X2: relative intensity of $n^{th}$ peak among theoretical isotope peaks;
Y2: relative intensity of $n^{th}$ peak among experimentally obtained isotope peaks;
C1: constant value; and
C2: constant value).

In step 4 of the above method, the database is preferably established from glycoproteins by using theoretical isotopic distribution of glycopeptides, but not always limited thereto.

In step 5 of the above method, similarity of the mass distribution of isotopes is preferably measured by using Euclidean distance and similarity of the strength distribution is preferably measured by using Pearson correlation analysis in order to produce S-score, but not always limited thereto.

In step 6 of the above method, Y-scoring is the process of confirming and evaluating the theoretical fragmentation of glycopeptide in tandem spectrum (CID and HCD). Herein, the said Y-score can be calculated by the following mathematical formula 3:

$$Y_{Score} = \frac{n}{N} * \sum_{i=1}^{n} \log_2\left(\frac{I_{[i]}}{I_{max}}\right) / (MassError + 1.0)$$ [Mathematical Formula 3]

(N: the number of observable glycopeptide fragmentation;

n: the number of observed glycopeptide fragmentation; and $I_i$: $i^{th}$ intensity in repetitive analysis).

In step 6 of the above method, tandem spectrum is HCD spectrum, and Y'-score is preferably calculated by the following mathematical formula 4, but not always limited thereto.

$$Y'\text{-score} = Y\text{-score} + y\text{-score}$$ [Mathematical Formula 4]

In this invention, y-score is calculated based on the theoretical distributions of b and y ions of peptides. Y'-score is the sum of Y-score and y-score.

In step 6 of the above method, tandem spectrum is ETD spectrum, and E-score is preferably calculated by the following mathematical formula 5, but not always limited thereto.

$$E_{Score} = \frac{n}{N} * \sum_{i=1}^{n} \log_2\left(\frac{I_{[i]}}{I_{max(ProcursorIonExclusion)}}\right) / (MassError + 1.0)$$ [Mathematical Formula 5]

(N: the number of observable glycopeptide fragmentation (c,z ions);

n: the number of observed glycopeptide fragmentation; and $I_i$: $i^{th}$ intensity in repetitive analysis).

In step 6 of the above method, family N-glycopeptide is additionally predicted based on the glycopeptide accurately identified by using tandem spectrum (MS/MS). The identification and quantification of glycopeptide is preferably performed without tandem spectrum (MS/MS) but using S-score and MS accuracy in MS1, but not always limited thereto.

In this invention, the present inventors presented the results of the identification and quantification of glycopeptides of the standard glycoprotein sample (RNaseB) by using HCD and CID spectrums obtained by high resolution mass spectrometer Orbitrap in Table 1.

TABLE 1

| Index | Glycopeptide | Retention Time | m/z | charge | spctraCount | DataPoint | Area |
|---|---|---|---|---|---|---|---|
| 1 | NLTK_5_2_0_0 | 48.09 | 846.358 | 2 | 3 | 13 | 225582363 |
| 2 | NLTK_6_2_0_0 | 47.96 | 927.384 | 2 | 6 | 22 | 142788155 |
| 3 | NLTK_7_2_0_0 | 47.96 | 1008.410 | 2 | 3 | 19 | 59502538 |
| 4 | NLTK_8_2_0_0 | 47.71 | 1089.436 | 2 | 16 | 20 | 89037692 |
| 5 | NLTK_9_2_0_0 | 47.46 | 1170.463 | 2 | 2 | 11 | 41747091 |
| 6 | NLTKDR_4_2_0_0 | 48.24 | 900.895 | 2 | 0 | 2 | NA |
| 7 | NLTKDR_5_2_0_0 | 48.36 | 981.921 | 2 | 0 | 4 | NA |
| 8 | NLTKDR_6_2_0_0 | 48.09 | 1062.948 | 2 | 1 | 6 | NA |

Figure 6A:
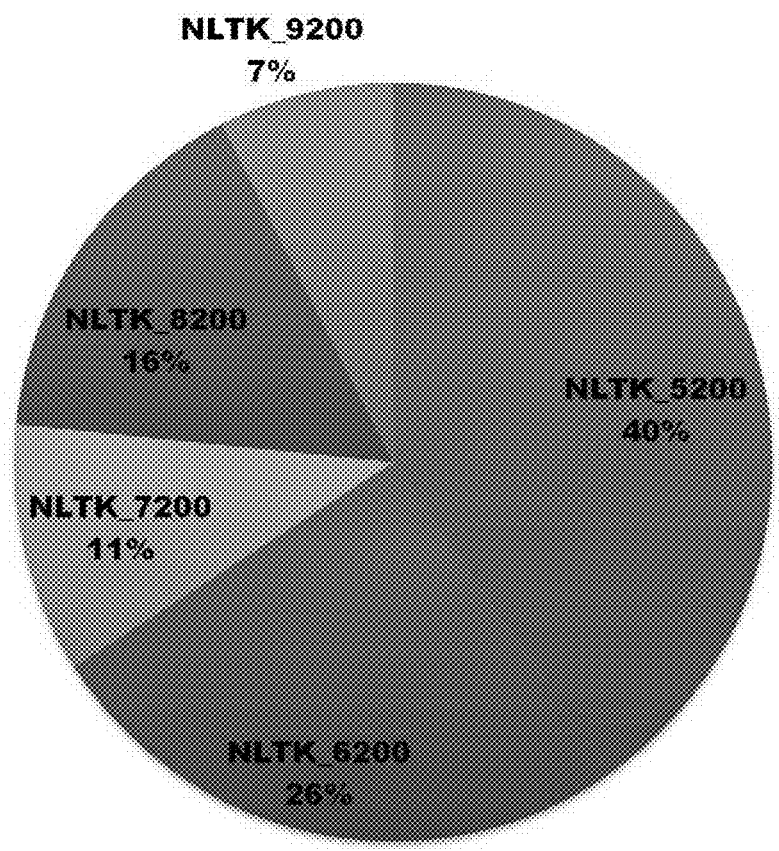
FIG. 6a is a diagram illustrating the pie graph presenting the relative amount of the glycopeptide quantified in step 7 of the bioinformatics platform for identification and quantification of N-linked glycopeptide of Example 1 performed with the standard glycoprotein.
Figure 6B:
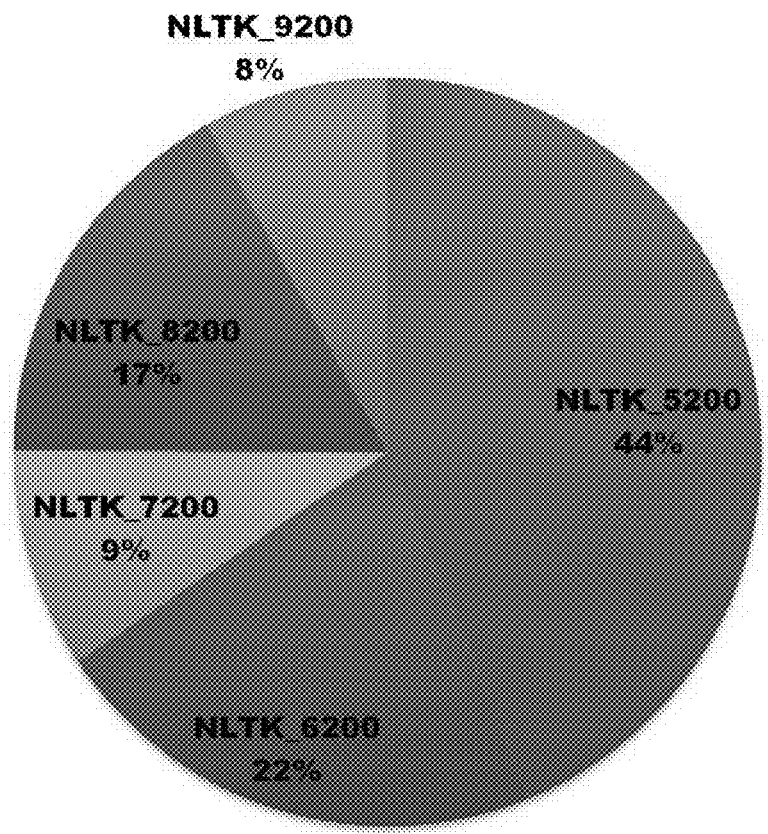
FIG. 6b is a diagram illustrating the pie graph presenting the relative amount of the glycopeptide quantified in step 7 of the bioinformatics platform for identification and quantification of N-linked glycopeptide of Example 2 performed with the standard glycoprotein.

In step 7, quantitative analysis is performed with the glycopeptides identified accurately by using the standard glycoprotein (RNaseB). The said quantitative analysis is performed by calculating area in ion chromatograms of each glycopeptide. Each data point for the calculation of area is the sum of three strongest isotope peaks. In the case that the number of data point is at least 7, gaussian distribution is applied and the area of the distribution is calculated and presented as quantitative value. Quantitative distribution of the standard glycoprotein sample (RNaseB) is presented as Venn diagram in FIG. 6a. As shown in FIG. 6a, NLTK_5200 (5Hex 2HexNac) was 40%, NLTK_6200 (6Hex 2HexNac) was 26%, NLTK_8200 (8Hex 2HexNac) was 16%, NLTK_7200 (7Hex 2HexNac) was 11%, and NLTK_9200 (9Hex 2HexNac) was 7%. The above quantitative distribution was consistent with that in a reference (Kathryn R. Rebecchi., et., al; Label-Free Quantitation: A New Glycoproteomics Approach. J. Am. Soc. Mass. Spectrom, 2009, 20, 1048-1059). Additional identification and quantification of glycopeptides were performed via correlation analysis with the identified glycopeptides without using MS/MS. MS2 spectrum (Spectra Count) zero in Table 1 is the example of the additional identification and quantification of glycopeptides. In example 2, the identification and quantification of glycopeptides of the standard glycoprotein sample (RNase B) was performed by using HCD and ETD spectrum obtained by high resolution mass spectrometer Orbitrap, and the results are shown in Table 2. As shown in FIG. 6b, similar quantitative distributions to the above were confirmed (NLTK_6200 (6Hex 2HexNac) was 22%, NLTK_8200 (8Hex 2HexNac) was 17%, and NLTK_7200 (7Hex 2HexNac) was 9%), which are presented in Table 2.

TABLE 2

| Index | Glycopeptide | Retention Time | m/z | charge | spctraCount | DataPoint | Area |
|---|---|---|---|---|---|---|---|
| 1 | NLTK_5_2_0_0 | 47.84 | 846.358 | 2 | 3 | 10 | 292355774 |
| 2 | NLTK_6_2_0_0 | 47.99 | 927.384 | 2 | 7 | 14 | 145015896 |
| 3 | NLTK_7_2_0_0 | 47.53 | 1008.410 | 2 | 1 | 11 | 63240833 |
| 4 | NLTK_8_2_0_0 | 47.16 | 1089.436 | 2 | 10 | 12 | 112879581 |
| 5 | NLTK_9_2_0_0 | 47.37 | 1170.463 | 2 | 2 | 9 | 53643120 |
| 6 | NLTKDR_4_2_0_0 | 47.86 | 900.895 | 2 | 0 | 2 | NA |
| 7 | NLTKDR_5_2_0_0 | 48.10 | 981.921 | 2 | 1 | 4 | NA |
| 8 | NLTKDR_6_2_0_0 | 47.84 | 1062.948 | 2 | 1 | 3 | NA |
| 9 | NLTKDR_7_2_0_0 | 47.64 | 1143.974 | 2 | 0 |  | NA |

Figure 7A:
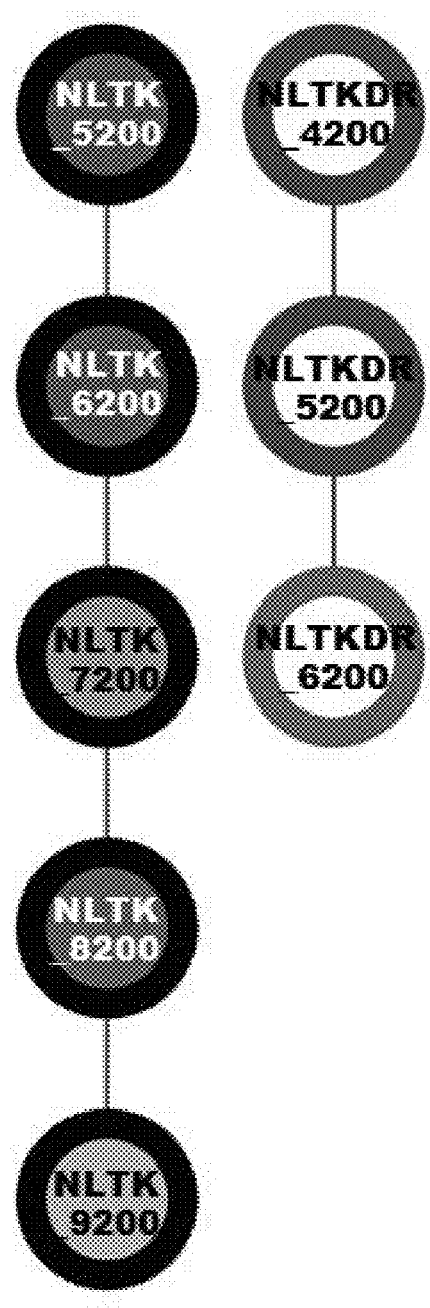
FIG. 7a is a diagram illustrating the correlation map obtained by correlation analysis of glycopeptide in step 8 of the bioinformatics platform for the identification and quantification of N-linked glycopeptide of Example 1 performed with the standard glycoprotein. The relative amount of glycopeptide is presented in red scale in node and the rim color is based on spectrum count. As shown in Table 1, when the number of tandem mass spectra count is 0, the color shows green, and when the number of tandem mass spectra count is 1, the color shows gray. Likewise, when the number is 2 or more, the color shows black.
Figure 7B:
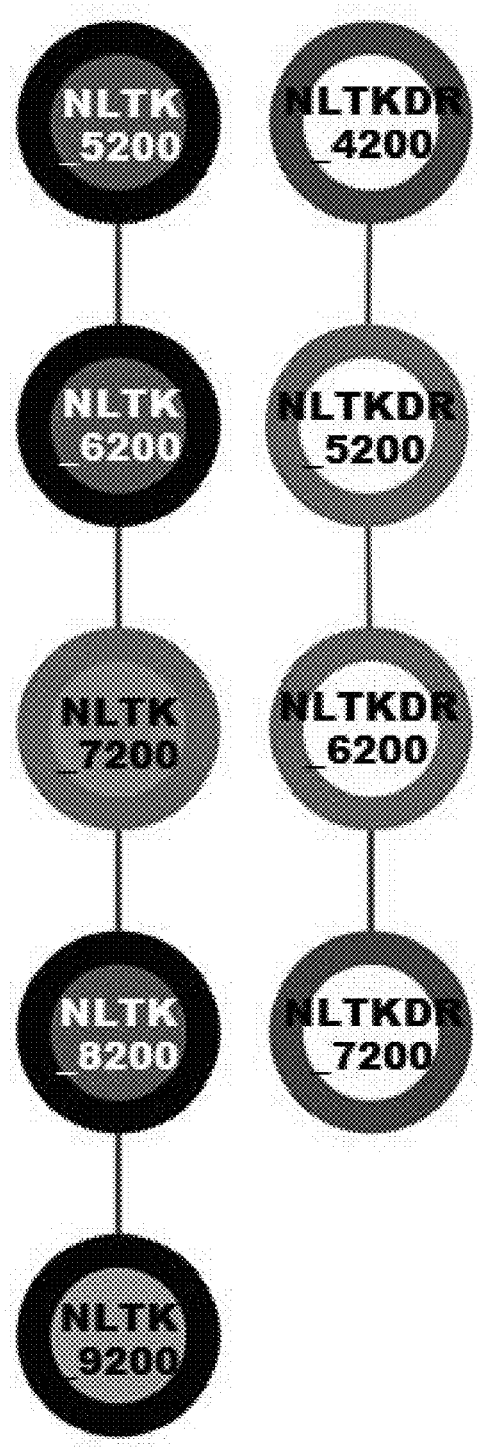
FIG. 7b is a diagram illustrating the correlation map obtained by correlation analysis of glycopeptide in step 8 of the bioinformatics platform for the identification and quantification of N-linked glycopeptide of Example 2 performed with the standard glycoprotein. The relative amount of glycopeptide is presented in red scale in node and the rim color is based on spectrum count. As shown in Table 2, when the number of tandem mass spectra count is 0, the color shows green, and when the number of tandem mass spectra count is 1, the color shows gray. Likewise, when the number is 2 or more, the color shows black.
Figure 8:
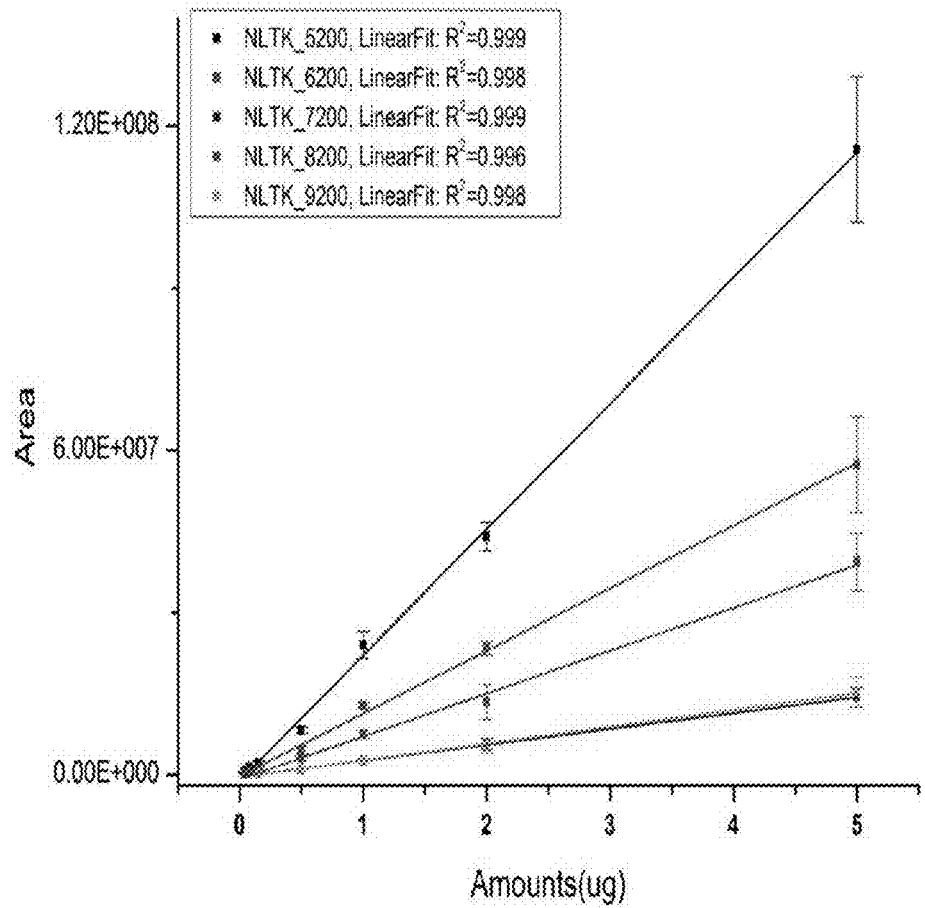
FIG. 8 is a diagram illustrating the quantification of glycopeptide over the concentration in RNase B (Ribonuclease B) confirmed in the mixed sample of Example 3.
Figure 9:
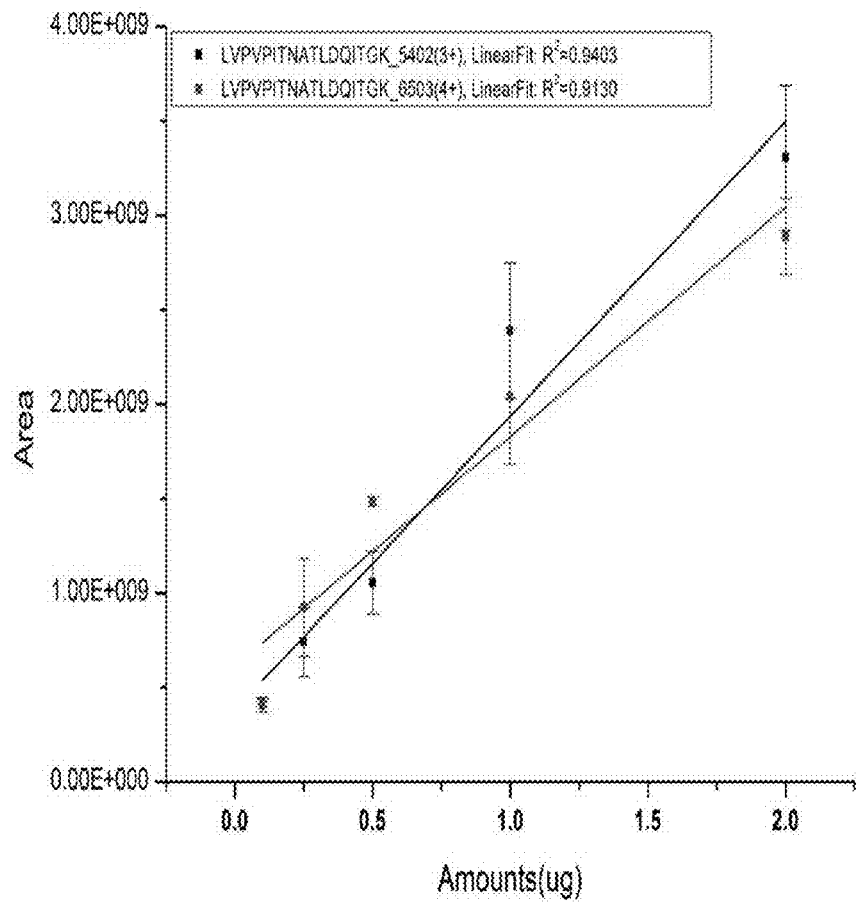
FIG. 9 is a diagram illustrating the quantification of glycopeptide over the concentration in AGP (Alpha1-Acid Glycoprotein) spiked in plasma as shown in Example 4.

In conclusion, the method of the present invention facilitates accurate identification and quantification of glycopeptides from the standard glycoprotein sample. The results of the qualitative analysis and quantitative analysis with glycopeptides performed in examples 1 and 2 are presented as correlation maps as shown in FIG. 7a and FIG. 7b. The results can be easily compared by comparing those maps. This method can be applied in many different attempts to analyze glycoprotein, and it is particularly expected to be very useful in the field of biosimilar.

In the present invention, the standard glycoprotein sample was analyzed with mass spectrometer Orbitrap, but not always limited thereto.

In the present invention, database was established with 281 glycoproteins found in human serum, but not always limited thereto.

In the present invention, glycosylations of only 350 sugars were considered, but not always limited thereto.

In the above method, the step of analyzing the correlation among glycopeptides and mapping the similarity among the samples for comparison is additionally added after the identification and quantification in step 8, but not always limited thereto.

In the above method, the enzyme used for hydrolysis is selected from the group consisting of trypsin, Arg-C, Asp-N, Glu-C, Lys-C, and chymotrypsin, but not always limited thereto.

In the above method, the mass spectrometer used herein is selected from the group consisting of LTQ-FT, Orbitrap, Triple-Tof, Q-Tof, and QExactive, but not always limited thereto.

In the above method, the identification and quantification is performed by using the high resolution mass spectrometer with mass resolution of at least 10,000 and mass accuracy of up to 50 ppm, but not always limited thereto.

In the above method, glycopeptide for the quantification is selected by using S-score in MS1 spectra, but not always limited thereto.

In the above method, the strength of the glycopeptide selected from MS1 spectra for the quantification is presented as the sum of the strength of three strongest peaks theoretically expected, but not always limited thereto.

The glycoprotein herein is preferably extracted from serum, plasma, blood, urine, cerebrospinal fluid, amniotic fluid, synovial fluid, or lavage fluid, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

EXAMPLE 1

Sample Preparation and Qualitative/Quantitative Analysis of Glycopeptide

The standard glycoprotein samples, RNase B (Ribonuclease B) and AGP (Alpha1-Acid Glycoprotein), were purchased from Sigma-Aldrich. The said two samples were mixed as shown in Table 3.

TABLE 3

| Sample No. | 1 | 2 | 3 | 4 | 5 | 6 | 7 |
|---|---|---|---|---|---|---|---|
| RNase B | 0.0375 μg | 0.075 μg | 0.15 μg | 0.5 μg | 1.0 μg | 2.0 μg | 5.0 μg |
| AGP | 0.15 μg | 0.15 μg | 0.15 μg | 0.15 μg | 0.15 μg | 0.15 μg | 0.15 μg |

Each sample was hydrolyzed with trypsin at 37° C. for overnight.

The polypeptides prepared by the above sample preparation process proceeded to high resolution mass spectrometer Orbitrap (Thermo Finnigan), followed by LC/ESI-MS/MS. To examine reproducibility of each sample, the analysis was repeated three times. The mass spectrometer RAW file was converted to ms1 (TXT) and ms2 (MGF) files by using the freeware program RawExtractor v1.9 (The Scripps Research Institute, La Jolla, Calif.) and MM File Conversion Tools v3.9 (www.massmatrix.net/mm-cgi/downloads.py). Identification and quantification of glycopeptides of RNase B was performed based on each mass spectrometry result by using the novel bioinformatics platform for the identification and quantifications of N-linked glycopeeptide of the present invention.

EXAMPLE 2

Sample Preparation and Qualitative/Quantitative analysis Of Glycopeptide

The standard glycoprotein sample AGP (Alpha1-Acid Glycoprotein) was purchased from Sigma-Aldrich. 6 high concentrated proteins were eliminated from plasma. The sample mix was prepared by spiking AGP in plasma as shown in Table 4.

TABLE 4

| | Sample No. | | | | |
|---|---|---|---|---|---|
| | 1 | 2 | 3 | 4 | 5 |
| AGP | 0.1 µg | 0.25 µg | 0.5 µg | 1.0 µg | 2.0 µg |
| Depleted plasma | 1.0 µg | 1.0 µg | 1.0 µg | 1.0 µg | 1.0 µg |

The polypeptides prepared by the above sample preparation process proceeded to high resolution mass spectrometer Orbitrap (Thermo Finnigan), followed by LC/ESI-MS/MS. To examine reproducibility of each sample, the analysis was repeated three times. The mass spectrometer RAW file was converted to ms1 (TXT) and ms2 (MGF) files by using the freeware program RawExtractor v1.9 (The Scripps Research Institute, La Jolla, Calif.) and MM File Conversion Tools v3.9 (www.massmatrix.net/mm-cgi/downloads.py). Identification and quantification of glycopeptides of AGP was performed based on each mass spectrometry result by using the novel bioinformatics platform for the identification and quantification of N-linked glycopeptide of the present invention.

INDUSTRIAL APPLICABILITY

As explained hereinbefore, the present invention can be effectively used for the development and examination of a novel biomarker for cancer diagnosis, and further can be effectively applied to biosimilar technique facilitating the analysis of glycopeptide and glucose structure of glycoprotein biotherapeutics.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A bioinformatics process for the identification and quantification of N-linked glycopeptide from glycoprotein, which comprises the following steps:
   obtaining mass spectrum by analyzing polypeptides prepared by hydrolyzing glycoproteins with protease by using high resolution mass spectrometer (step 1);
   converting the mass spectrum obtained in step 1 into MS1 (Mass spectrum 1) and tandem spectrum (MS/MS) (step 2);
   calculating M-score at each tandem spectrum selected from the group consisting of converted tandem spectrums showing Oxonium ion peak molecular weights of 129.06, 138.06, 145.05, 147.07, 163.06, 168.07, 186.08, 204.08, 274.09, 292.10, 350.15, 366.14, 454.16, 528.19, and 657.24 (step 3), wherein the M-score is calculated by the following mathematical formula 1:

[Mathematical Formula 1]

$$M_{Score} = \frac{n}{N} * \frac{\sqrt{\sum_{i=1}^{n} O_i}}{(n-1)}$$

$$O_i = \frac{I_i}{I_{max(<700Da)}} * C / MassError + 1.0$$

(N: Number of observable oxonium ions;
n: number of observed oxonium ions,
$I_i$: $i^{th}$ peak intensity in repetitive analysis; and
C: constant value);
selecting glycopeptide spectrum using the M-score obtained in step 3 (step 4);
obtaining isotopic distribution in MS1 of the glycopeptide spectrum selected in step 4, which is compared with a database to calculate S-score, and then identifying glycopeptide candidates by using the calculated S-score (step 5), where the S-score is a calculation for the comparison of similarity of the theoretically isotopic distribution obtained from the database with the isotopic distribution obtained by experiment with MS1, and wherein the S-score is calculated by the following mathematical formula 2:

[Mathematical Formula 2]

$$S_{Score} = \left(\frac{1.0}{\left[1.0 + \sum_{i=1}^{n}(X1-Y1)_i^2\right]} * C1\right) + \left(\frac{n(\sum X2Y2) - (\sum X2)(\sum Y2)}{\sqrt{(n\sum X2^2 - (\sum X2)^2) * (n\sum Y2^2 - (\sum Y2)^2)}} * C2\right)$$

(X1: mass of $n^{th}$ peak among theoretical isotope peaks;
Y1: mass of $n^{th}$ peak among experimentally obtained isotope peaks;
X2: relative intensity of $n^{th}$ peak among theoretical isotope peaks;
Y2: relative intensity of $n^{th}$ peak among experimentally obtained isotope peaks;
C1: constant value; and
C2: constant value);
evaluating exact glycopeptide from the glycopeptide candidates identified in step 5 by using E-score, Y-score, and Y'-score in tandem spectrum (step 6),
wherein the E-score is calculated by the following mathematical formula 5:

[Mathematical Formula 5]

$$E_{Score} = \frac{n}{N} * \sum_{i=1}^{n} \log_2\left(\frac{I_{[i]}}{I_{max(ProcursorIonExclusion)}}\right) \Big/ (MassError + 1.0)$$

(N: the number of observable glycopeptide fragmentation (c,z ions);
n: the number of observed glycopeptide fragmentation; and
$I_i$: $i^{th}$ intensity in repetitive analysis) spectrum;

wherein the Y-score is calculated by the following mathematical formula 3:

$$Y_{Score} = \frac{n}{N} * \sum_{i=1}^{n} \log_2\left(\frac{I_{[i]}}{I_{max}}\right) / (MassError + 1.0)$$ [Mathematical Formula 3]

(N: the number of observable glycopeptide fragmentation;
n: the number of observed glycopeptide fragmentation; and
$I_i$: $i^{th}$ in repetitive analysis); and wherein the Y'-score is calculated by the following mathematical formula 4:

Y'-score=Y-score+y-score;  Mathematical Formula 4 performing quantitative analysis with the glycopeptides evaluated in step 6 (step 7); and
performing additional identification and quantification of family N-linked glycopeptide via correlation analysis with those glycopeptides quantified in step 6 (step 8).

2. The bioinformatics process for the identification and quantification of N-linked glycopeptide from glycoprotein according to claim 1, wherein the tandem spectrum is CID or HCD spectrum.

3. The bioinformatics process for the identification and quantification of N-linked glycopeptide from glycoprotein according to claim 1, wherein the database is established in step 4 from glycoproteins by using theoretical isotopic distribution of glycopeptides.

4. The bioinformatics process for the identification and quantification of N-linked glycopeptide from glycoprotein according to claim 2, wherein the similarity of the mass distribution of isotopes is measured by using Euclidean distance and the similarity of the strength distribution is measured by using Pearson correlation analysis in order to produce S-score in step 5.

5. The bioinformatics process for the identification and quantification of N-linked glycopeptide from glycoprotein according to claim 1, wherein the tandem spectrum in step 6 is CID or HCD spectrum.

6. The bioinformatics process for the identification and quantification of N-linked glycopeptide from glycoprotein according to claim 1, wherein the tandem spectrum in step 6 is HCD spectrum.

7. The bioinformatics process for the identification and quantification of N-linked glycopeptide from glycoprotein according to claim 1, wherein the tandem spectrum in step 6 is ETD spectrum.

8. The bioinformatics process for the identification and quantification of N-linked glycopeptide from glycoprotein according to claim 1, wherein the glycopeptide is identified and quantified without tandem spectrum (MS/MS) but using S-score and MS accuracy in MS1 after the family N-glycopeptide is additionally predicted based on the glycopeptide accurately identified by using tandem spectrum (MS/MS) in step 6.

9. The bioinformatics process for the identification and quantification of N-linked glycopeptide from glycoprotein according to claim 1, wherein the correlation of all the glycopeptides is presented as a map representing the similarity among the samples for comparison after the identification and quantification in step 8.

10. The bioinformatics process for the identification and quantification of N-linked glycopeptide from glycoprotein according to claim 1, wherein the hydrolysis is performed by using the enzyme selected from the group consisting of trypsin, Arg-C, Asp-N, Glu-C, Lys-C, and chymotrypsin.

11. The bioinformatics process for the identification and quantification of N-linked glycopeptide from glycoprotein according to claim 1, wherein the mass spectrometer is the one selected from the group consisting of LTQ-FT, Orbitrap, Triple-Tof, Q-Tof, and QExactive.

12. The bioinformatics process for the identification and quantification of N-linked glycopeptide from glycoprotein according to claim 1, wherein the identification and quantification is performed by using the high resolution mass spectrometer with mass resolution of at least 10,000 and mass accuracy of up to 50 ppm.

13. The bioinformatics process for the identification and quantification of N-linked glycopeptide from glycoprotein according to claim 1, wherein the glycopeptide for the quantification is selected by using S-score in MS1 spectra.

14. The bioinformatics process for the identification and quantification of N-linked glycopeptide from glycoprotein according to claim 1, wherein the strength of the glycopeptide selected from MS1 spectra for the quantification is presented as the sum of the strength of three strongest peaks theoretically expected.

* * * * *